(12) United States Patent
Urfig

(10) Patent No.: US 6,630,110 B2
(45) Date of Patent: Oct. 7, 2003

(54) METHOD AND APPARATUS FOR SPECIALIZED CANDLE

(75) Inventor: Bernard Ilon Urfig, Studio City, CA (US)

(73) Assignee: Global Aromatics, Inc., Concord, CA (US)

( * ) Notice: Subject to any disclaimer, the term of this patent is extended or adjusted under 35 U.S.C. 154(b) by 328 days.

(21) Appl. No.: 09/809,945

(22) Filed: Mar. 14, 2001

(65) Prior Publication Data

US 2002/0131909 A1 Sep. 19, 2002

(51) Int. Cl.[7] .................................. A62B 7/08
(52) U.S. Cl. .................. 422/125; 422/123; 431/126; 431/288; 431/289
(58) Field of Search ................ 422/1, 123, 125; 431/126, 288, 289; D26/6

(56) References Cited

U.S. PATENT DOCUMENTS 5,927,965 A * 7/1999 Pappas ........................ 431/289

FOREIGN PATENT DOCUMENTS

DE          3640644 A    *  6/1988

* cited by examiner

Primary Examiner—Robert J. Warden, Sr.
Assistant Examiner—Sean E. Conley

(57) ABSTRACT

The improved method and apparatus for scented candle, is provided using a specifically sized and prepared candle body. In the preferred embodiment of the present invention, the candle body is uniformly an elongated cylinder. In the preferred embodiment, three vertical shafts are added to the set, specifically sized cylindrical candle body: (i) one shaft is a centrally drilled hole to a specified depth; (ii) a second shaft is a hole drilled off-center, to a specified depth; and (iii) a third shaft is a hole drilled into the center of the second shaft from the end of the second-shaft, specified depth through the bottom of the candle. A wick is inserted into the centrally drilled shaft. A heat conductive vial is inserted into the second shaft, with the vial open end directionally facing up towards and above the candle top. The vial is filled with a preselected fluid, such as fragrance oil. The top of the vial is sleeved and capped until the end user removes it in the process of lighting and enjoying the scented candle apparatus. The candle wax coloration and vial sleeve coloration are matched to relate to the scent or fragrance placed into the vial.

10 Claims, 3 Drawing Sheets

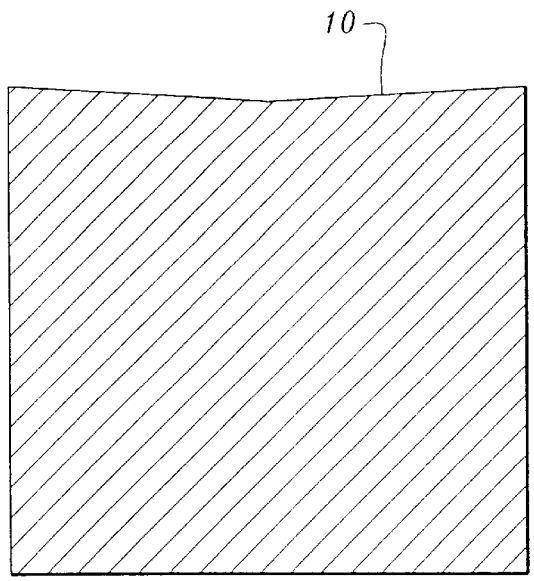
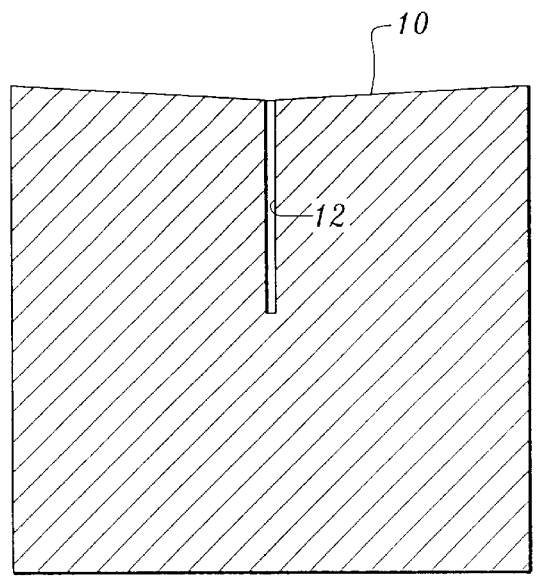
Fig. 1
Fig. 2
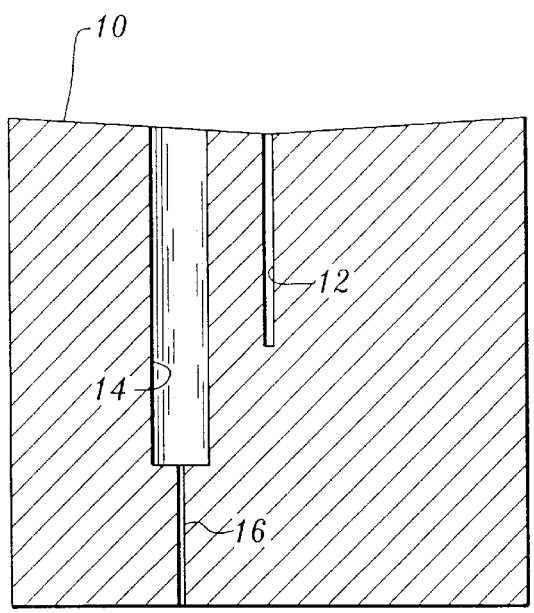
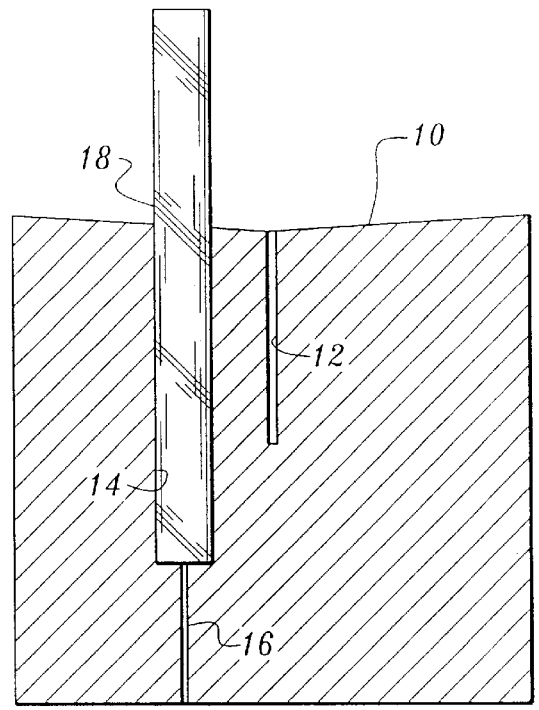
Fig. 3
Fig. 4

METHOD AND APPARATUS FOR SPECIALIZED CANDLE

CROSS-REFERENCES TO RELATED APPLICATIONS

None.

STATEMENT REGARDING FEDERALLY SPONSORED RESEARCH OR DEVELOPMENT

None.

REFERENCE TO A MICRO-FICHE APPENDIX

None.

BACKGROUND OF THE INVENTION

1. Field of the Invention

This invention relates to specialized candles. More particularly, the preferred embodiment of this invention relates to a candle-like product and method which provides a sustained and uniformly noticeable scent or aroma to the user when the candle is lighted.

2. Description of the Related Art including Information Disclosed under 37 C.F.R. 1.97 and 1.98

There are various methods and products intended to provide a candle which when lighted provides a uniformly controlled dispersal of a desired ingredient, such as fragrance in the context of scented candles or insect repellant in the context of specialty candles. For the most part, these candles have mixed the intended special materials with molten wax to produce as close to a homogenous mixture as possible. This mixture is then molded or otherwise shaped in conformity with methods known in the art to produce candles with special characteristics. Most notable in these efforts are aromatic, scented, or fragrant candle products.

The prior art includes use of surrounding a candle central wick with odorizing chips, mixing the paraffin or other candle wax with ethers or oils containing a selected fragrance, or using gels or oils as a portion of the candle body in direct contact with the burning wick of the candle.

These prior art scented candles are limited in many respects. First, the combined mixing of scented oils and paraffin yields unsatisfactory delivery of fragrance. Fragrance oils are not soluble in candle wax. Fragrance delivery in these mixed candles is impeded by the differing physical properties between the oils and paraffin, since the oils are heavier and over time sink to the candle bottom. After such migration of the fragrance to the bottom of the candle, little or no scent is provided upon lighting the candle while a very strong scent remains when the candle wick has burned out.

Use of gels or other external fragrance bases or carrier yield an unsatisfactory product from the standpoint of excessive heat or flashing when the candle is burned for long periods of time.

Other attempts to overcome the separation of oil and paraffin and gravitational migration of the oil to the candle bottom include using paraffin of differing densities, with the paraffin containing a higher percentage of scented oil either being perpendicularly or vertically aligned with the candle's main vertical axis and inserted through the candle. This approach provides no discernable benefit since the main paraffin composition constantly remains above the denser wax. In fact, this approach emits a stronger scent when the candle is unlit since the main candle wax has not shrouded the more fragrant plug insert. These approaches also increase production costs without any real product improvement.

In view of the above, there is a need for an improved method and apparatus for scented candle which overcomes the problems and limitations of the prior art.

BRIEF SUMMARY OF THE INVENTION

The present invention relates to an improved method and apparatus for scented candle which provides a controlled and evenly sustained release of a desired ingredient such as fragrance, natural scents, phenomones, insect repellents, and the like within an aesthetically pleasing candle product appearance.

In addition to above described scented candle, the method of making that candle is also disclosed as including the steps of: forming an elongated cavity within the body of a standard wax candle and providing a tube within said cavity in which a desired fragrance or scent is housed.

It is an object of the present invention to provide an economical scented candle which will deliver a uniform fragrance or aroma over the life of the fragrance in said tube.

It is a further object of the present invention to provide a candle wherein the fragrance does not segregate or stratify within the candle body.

It is yet a further objective of the present invention to provide a new and useful fragrant or scented candle and method for making the same.

It is yet a further objective of the present invention to provide a candle that enhances fragrance life over scented candles in the existing art.

It is still another objective of the present invention to provide as much fragrance over the burning life of a candle as possible.

Other features, advantages, and objects of the present invention will become apparent with reference to the following description and accompanying drawings.

BRIEF DESCRIPTION OF DRAWINGS

FIG. 1 is a cross-sectional view of the candle body of the preferred embodiment of the present invention.

FIG. 2 is a cross-sectional view of the candle body of the preferred embodiment of the present invention depicting the center drilled hole.

FIG. 3 is a cross-sectional view of the candle body of the preferred embodiment of the present invention depicting the center drilled hole, the off-center drilled hole, and the smaller continuation of the off-center drilled hole continuing through the candle bottom.

FIG. 4 is a cross-sectional view of the candle body of the preferred embodiment of the present invention depicting the three drilled holes of FIG. 3 with the glass vial of the preferred embodiment of the present invention inserted into the off-center drilled hole.

DETAILED DESCRIPTION OF THE INVENTION

Referring more particularly to the drawings, FIG. 1 illustrates a cross-section of a specialized candle body 10 of the present invention. To prepare the preferred embodiment of the specialized candle according to the principles of the present invention, the candle body should be formed by pouring candle wax into an approximate mold width of 2¾ inches to a height of 2-½ inches. The poured candle body 10 wax is required to set completely before any of features of the preferred embodiment of present invention are added. However, these critical features may be installed as part of the manufacturing process for other embodiments of the present invention, and should not be limited by the preferred method of making the preferred embodiment of the present invention. Once the candle body 10 has completely set, it should have sunk in slightly at the top, to achieve a slight concavity, as shown by FIG. 1. Any candle waxes known in the art, such as paraffin, bees wax, or the like, are suitable materials for the candle body 10. Again, the principles of the present invention do not require concavity of the candle top; however, fragrance life is maximized using the concave candle top of the preferred embodiment.

Figure 8:
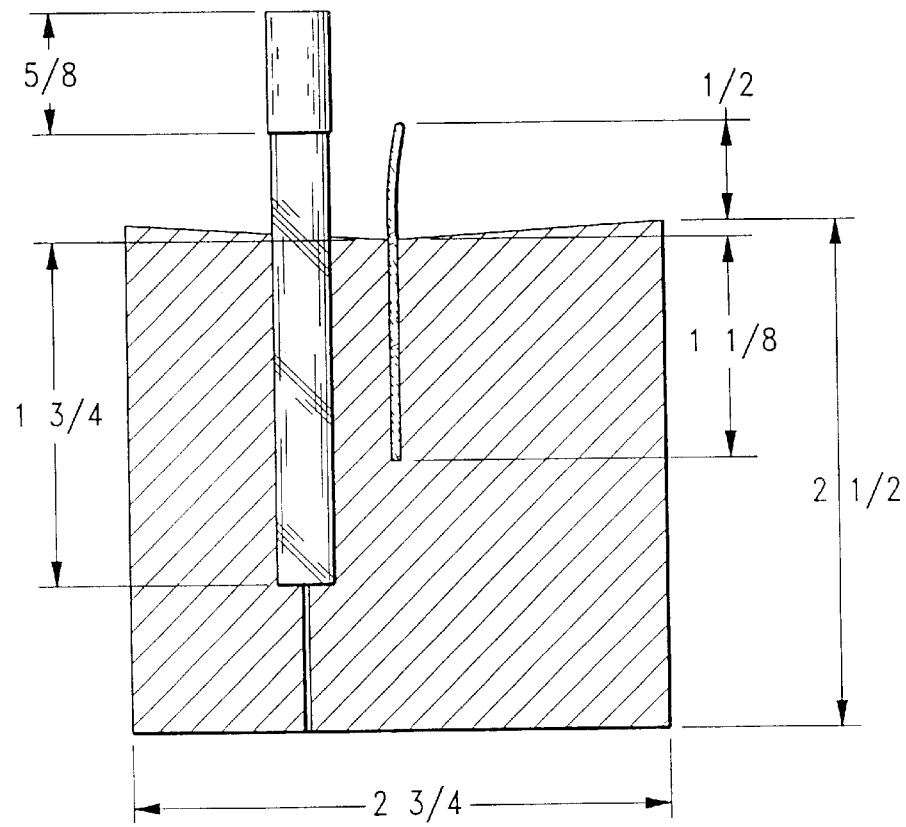
FIG. 8 is a cross-sectional view of the dimensions of the preferred embodiment of the present invention.
Figure 9:
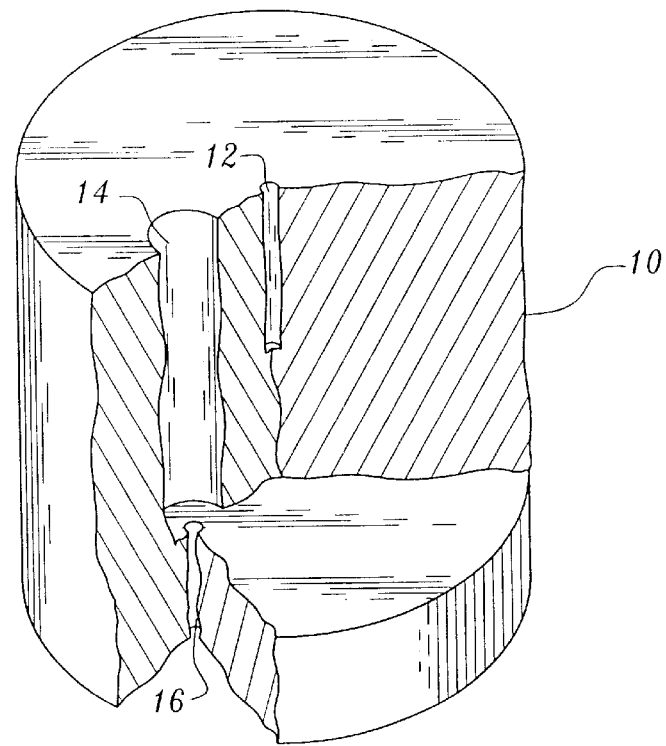
FIG. 9 is an isometric view of the preferred embodiment of the present invention partially broken away to show the critical features thereof.

Once the candle body 10 is set, it is already to have three holes or shafts drilled. As depicted in FIG. 2, in the preferred embodiment of the present invention, the first hole 12 should be drilled directly and straight down the central vertical axis of the candle body 10 by use of a balanced drill press, or similar means known in the art. It is vital that the drilled hole be perfectly straight, so that the candle wick that is placed within should burn with as much distance-consistency away from the added features of the preferred embodiment of the present invention as possible. For the preferred embodiment of the present invention, the diameter of this drilled hole should be drilled out with a 2 mm drill bit. The depth of this hole into the candle body 10 should not exceed 1⅛ inches as shown in FIG. 8.

As depicted in FIG. 3, the second hole in the candle body 10 for the preferred embodiment of the present invention is prepared for the glass vial, and should be drilled out at ¼ of an inch away from the centered hole 12. The size drill bit that should be used for this preferred embodiment of the present invention is recommended to be 7 mm. It is important to begin drilling this hole with the outside diameter of the drill bit ¼ inch away from the centered hole, so that when the two-drilled holes are complete, they will be ¼ of an inch away from each other. Do not mark a ¼ inch away from the centered hole and drill from the middle of the drill bit, because this will not give you a ¼ inch distance, which is required for the principles of the present invention. The depth of this second hole should be 1-¾ inches, as shown in FIG. 8. The same consistency of a straight hole should apply here, as mentioned above for the central hole 12 drilled for the candle wick.

The third step is providing the smallest and final hole 16 in the candle body 10 required for the preferred embodiment of the present invention. The purpose of this third hole 16 (beneath the 7 mm hole) is to allow air to be removed when gently forcing the glass vial 18 through. If this third hole 16 was not provided, the glass vial 18 would be automatically forced upwards from the 7 mm hole 14 due to the air pressure within the hole 14. The same or different 2 mm drill bit should be drilled directly through the bottom of the 7 mm hole 14, and completely through the candle body as depicted in FIG. 3. For the preferred method of making the preferred embodiment of the present invention, this third hole is aligned co-axially with the central axis of the 7 mm hole 14. The drill bit should be long enough to drill through, as the drilling point of this final hole 16 begins where the 7 mm hole 14 ends within the candle body 10. This third hole can be any diameter dimension smaller than the second hole. For ease in manufacturing method of the preferred embodiment of the present invention, this third hole width is set at 2 mm, and is co-axially aligned with the central axis of the 7 mm hole 14.

Once the three holes have been completed according to the specification of the preferred embodiment of the present invention as detailed above and depicted in FIGS. 3 and 4, the specialized candle body 12 is ready to have the glass vial 18 inserted as depicted in FIG. 4. Although the diameter of the glass vial 18 is 8 mm, and the hole 14 diameter is 7 mm, it is required to gently force the glass vial 18 down the hole 14 as far as it will go, allowing approximately 1 inch of the glass vial 18 exposed above the concave candle body 10 top. The reason for this technique is for the candle wax around the inserted glass vial 18 to firmly hold the glass vial 18 in place, so that the end user for safety purposes can no longer remove it accidently. By gently forcing the vial through the intended hole 14, the candle body 10 wax will expand slightly, without deformity to the candle body 10 shape, allowing the glass vial 18 to position firmly in place in the hole 14 of the candle body 10. Again, this is the requirement for the preferred embodiment of the present invention hole 14 diameter is 7 mm and the glass vial 18 diameter is 8 mm. Other dimensions are possible; but these are the preferred dimensions for maximum fragrance life. The expansion of the candle body 10 wax about the circumference of the glass vial 18 may differ slightly under different conditions and wax materials. In the event that such expansion deforms the candle body 10, then manufacture should adjust this method by adjusting the hole 14 diameter to adequately and firmly hold the glass vial 18 in place in accordance with the principles of the present invention.

Figure 5:
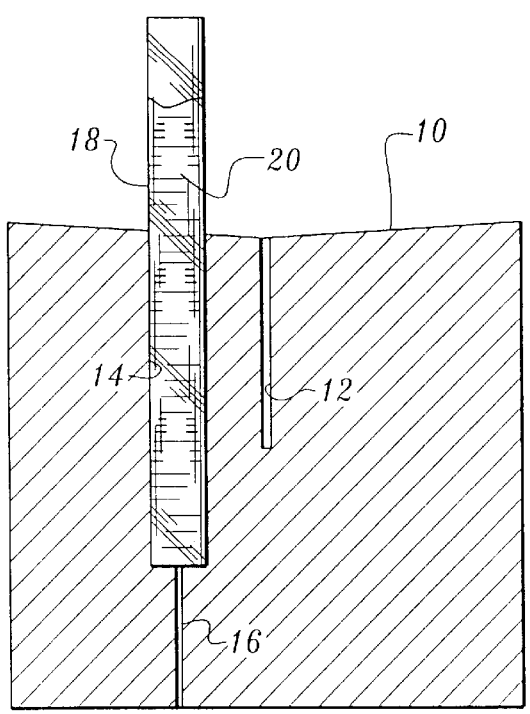
FIG. 5 is a cross-sectional view of the candle body of the preferred embodiment of the present invention depicting the three drilled holes with the glass vial of the preferred embodiment of the present invention as depicted in FIG.4 with fragrance contained in said glass vial.

As shown in FIG. 5, the next step in the preferred embodiment of the present invention requires the filling of the glass vial 18 with a preselected fragrance 20. The amount of fragrance 20 should almost fill the glass vial 18, leaving approximately 5 mm of the top of the glass vial 18 unfilled. The exact volume of fragrance 20 cannot be determined at this time, because the glass vial 18 needed for this embodiment of the present invention is custom cut. Although the exterior diameter of the glass vial 18 used in research and testing of the preferred embodiment will be exactly the same as the production order, the inner diameter of the vial may vary slightly. Since this interior glass vial 18 diameter variable only effects the volume of fragrance 20 required to fill the glass vial 18 to approximately 5 mm from the top of the glass vial 18, this exact fragrance volume is not necessarily critical to the principles of the present invention, and can be determined later.

Figure 6:
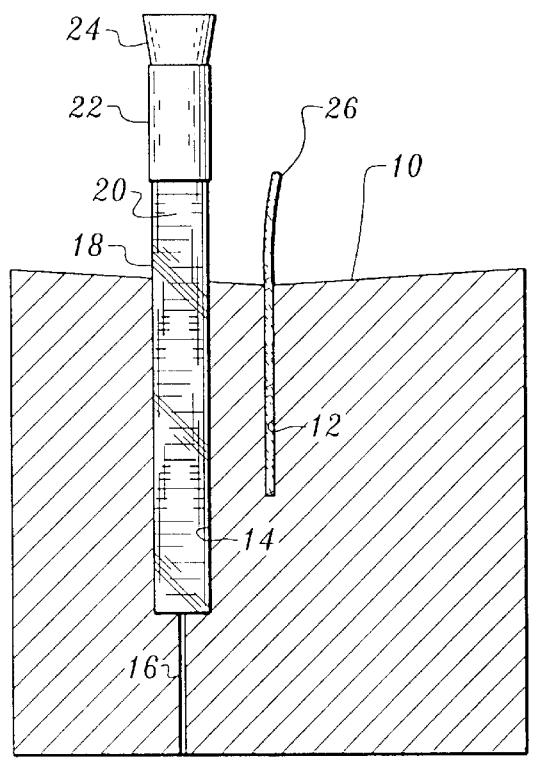
FIG. 6 is a cross-sectional view of the candle body of the preferred embodiment of the present invention as depicted in FIG.5 with the aluminum sleeve over the top of said glass vial and a cork inserted into open top end of said glass vial.

Once the glass vial 18 is securely in place in the designed hole 14, and filled with fragrance 20, as shown in FIG. 6 the top of the glass vial is banded with an aluminum tube 22. For the preferred embodiment of the present invention, the aluminum tube 22 should simply be placed over top portion of the glass vial 18, where it will indefinitely rest until removed, if desired by the end user. It is important to clean off any excess fragrance oils on the glass vial 18 exterior before the aluminum tube 22 is placed over the glass vial 18. This safety precaution should prevent any excess fragrance oil from being exposed to the open flame of the candle.

Once the aluminum tube 22 has been placed over the glass vial 18, the cork 24 or similar stopper should be firmly inserted into and sealing the open end of the glass vial 18, until the end user removes it. By removing the cork 24 and replacing it too often while the vial is still full, excess fragrance oil 20 will flow out the open glass vial 18 top and over the exterior sides of the glass vial 18, which is not recommended. The aluminum tube 22 that is placed over the glass vial 18 is colored to coordinate with, complement, and otherwise relate visually to the sent or fragrance of the specialized candle. For example; if the fragrance were peach, then the aluminum tube 22 should be orangish yellow, or similar shade of the natural fruit peach, in color.

Figure 7:
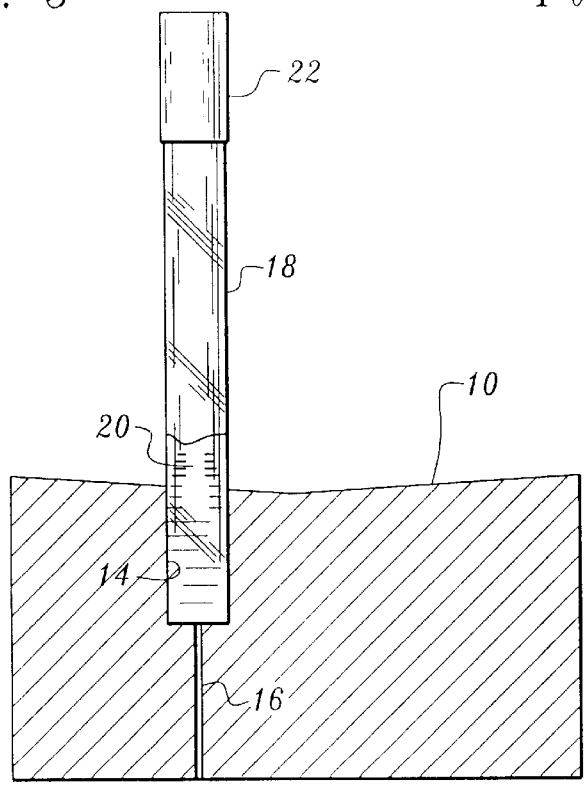
FIG. 7 is a cross-sectional view of the remaining candle of the preferred embodiment of the present invention once the wick has completely burned.

The final step to assemble the preferred embodiment of the present invention for specialty candle is to insert the wick 26 through the central axis hole 12 of the candle body 10. Before the wick 26 is inserted, it should be treated in wax, which enhances the ability to insert the wick 26 into the central axis hole 12. Once the wick 26 has been inserted, and cannot be pushed down any further, it should be trimmed to an exposed height of ½ inch above the concave top of the candle body 10, as shown in FIG. 8. This finished wick trim dimension allows the wick to continue burning as the candle body 10 wax around it begins to melt and quickly shortens the exposed wick to the desired length for optimal usage. The wick 26 for the preferred embodiment of the present invention is shorter than the standard candle wick lengths, because the wick 26 must end, or stop burning before it reaches the bottom of the glass vial 14. The reason for this is that once the candle body 10 has completely burned down with this specified wick 26 length, the glass vial 14 will still have an amount of candle body 10 wax supporting it, and keeping the glass vial 14 in vertical alignment with the candle body 10 central axis. Again, this is a safety issue as there may be an amount of fragrance oil 20 remaining in the glass vial 14, even when the candle has been completely used. The remaining candle body 10 wax acts like a base for the glass vial 14 at this point, as shown in FIG. 7.

The preferred embodiment of the present invention is a general candle, modified in the necessary methods to house a container filled with either an essential oil, or any other scented fragrance chosen by the manufacturer, that is suitable for this application. The specialized candle of the present invention is simply lit by the end user, as any general candle would be. Referring to FIG. 6, the lighted wick 26 heats up a container, or glass vial 14, that is placed close enough to the burning flame, so that the fragrance oil 20 within the container, or glass vial 14, emits a pungent odor into the atmosphere. By using this technique it is possible to maintain a high percentage of the fragrance utilized in this application, allowing the end user to experience a more noticeable effect compared to a standard candle, as a standard candle is limited to the amount of fragrance that can be used.

The specialized candle assembly instructions may appear to be timely or confusing in theory, however the manufacturing process should be relatively simple and efficient, when constructing the specialized candle of the present invention in production.

After extensive testing, the specialized candle of the present invention has evolved in numerous technical areas from the first prototype. Principally and physically, however, the specialized candle appears the same.

The objective in the first test prototypes was to maximize fragrance over time from the burning of a candle. Most candles offer this principle already, however the principal objective of the principles of the present invention was to enhance the fragrance that a standard candle would offer. Beginning with the initial test prototypes, noticeable enhancement was obtained by vertically inserting an aluminum tube, filled with an essential oil fragrance, down into the candle, approximately one half inch away from the centered wick. For these initial prototypes within a couple of minutes of lighting the candle wick the aluminum tube started to heat up quickly. In turn, the aluminum tube conducted heat to the essential oil fragrance within and the fragrance was naturally released into the atmosphere. It appeared that this principle could work, and certainly offered a strong scented aroma, which satisfied the main proto-type testing objective.

The prototyped candles were allowed to completely burn down, so that problems associated with the end of the candle life could be studied. As heat is applied to the aluminum tube, the heat could cause different, overall effects over time. There are noticeable problems after hours of burning. Since aluminum is a good heat conductor, the aluminum tube would enhance its own heat in areas that are not acceptable for the principles of the present invention. Once the lighted wick heated the aluminum tube placed inside the candle, the tube would radiate enough heat up to melt the candle wax around the entire tube. As the supporting candle wax around the aluminum tube softened, the vertical integrity of the tube was severely compromised. Testing was preformed on simple methods of preventing the aluminum tube from moving once it had melted the candle wax surrounding it. One such method was to attach the tube to a base that would hold the tube upright. This solution includes providing a solid aluminum base attached to the tube; however, the costs to produce or manufacture the tube on a stand is not acceptable. The cost of material was acceptable; however, the cost of labor and setups would far outweigh the acceptability of attaching the tube to a metal base. The base had to be made from metal, since non-metallic base materials attached to the heated aluminum tube could present safety issues.

Use of a metal base was abandoned in testing other means to support the aluminum tube while heated. One option was to plug or fill the bottom end of the tube with a non-metal substance, so that the heat generated down the tube would stop at the inserted plug. The inserted plug was to be inserted firmly inside the aluminum tube, but exposing the majority of the non-metallic plug. The plug would hold the tube upright supported by the candle wax around it. The plug used essentially an inverted cork design, with the cork bottom end wider than the top end, allowing half of the cork to be inserted into the aluminum tube, and the other end exposed. The candle wax would support the exposed part of the cork, because it is non-conductive, therefore allowing the candle wax around the cork to remain solid and support the vertical orientation of the aluminum tube.

This idea worked well, but presented additional production problems. Because the cork was wider at the bottom, once it was inserted into the aluminum tube the tube lost its uniform cylindrical dimensional form. Insertion of the aluminum tube fitted with the cork into the candle was difficult. Insertion would require a pre-drilled hole from the candle body bottom. The fitted aluminum tube is then forced upwards until the larger or exposed part of the cork would prevent it from moving any further, this solution required two holes for the tube. After drilling the initial hole to house the aluminum tube, a second and larger hole needed to be drilled at the bottom of the candle to accept insertion of the exposed and wider cork into the candle. Once the tube and cork were in place, there was a large hole beneath the candle, which had to filled again with wax. The necessity for filling the second hole was to stop the wax dripping or flowing down the side of the cork from the open area above it. The process of double drilling the candle body and refilling is too time consuming and not cost effective.

The manufacturing procedure required to produce the specialized candle of the present invention needs to be as simple and cost effective as possible. Generally speaking, candles are not expensive or long lasting items. Thus, every effort should be made to keep the manufacturing costs as low as possible, so that the candle can economically compete within this industry.

After experimenting with numerous ideas, the most practical, overall solution to the vial material would be to use a glass vial that would contain the chosen fragrance, instead of the aluminum tube. One advantage of the glass over aluminum is that it does not transfer heat as rapidly or intensely as aluminum. Another advantage is that a glass vial is manufactured inexpensively with an enclosed bottom. These two features of a glass vial eliminate the referenced function and production problems that would need to be overcome with use of an aluminum tube. Fortunately, the effect of the heat radiated from the lighted candle wick to the fragrance within a glass vial inserted into the candle body appears to function the same or similar as with the aluminum tube. It is simpler to drill one size hole or shaft into the candle body and insert the glass vial. Because the glass does not transfer heat as quickly or intensely, the glass vial remains in its vertically aligned position, being supported by the solid candle wax around it.

Using a glass vial to contain the fragrance oils presents a separate and distinct issue. The burning candle wick flame deposits an amount of carbon at the top of the glass vial once in place. This carbon deposit does not cause a functioning problem; however, it presents an suitable overall candle appearance. Various positions related to the burning candle wick flame were tested without much success in overcoming the carbon deposit on the glass vial top.

The most effective solution to the carbon deposit is to use a portion of aluminum tube fitted snugly over the top of the glass vial as a protective guard. The anodized aluminum tube top for the glass vial satisfies two different functions. First it provides a pleasing appearance coordinated in color to match the particular candle fragrance. Second, it protects the top of the glass from carbon deposits. Once being exposed to the candle wick burning flame, the aluminum gradually does discolor. This gradual discoloration occurs well into the burning life of the candle and does not present noticeable discoloration. Most standard candles deteriorate into the burning life of the candle. The specialized candle of the present invention allows replacement of these aluminum tube vial caps after a few hours of burning if the user so desires.

The positioning and length of the aluminum tube vial caps are not the same as the glass vial. The aluminum tube vial cap will cover approximately one quarter of the length of the vial. The reasons for this are to avoid the aluminum tube form burning the supporting wax as explained above. The aluminum tube vial cap must always remain at the top of the glass vial, even when it is use. Otherwise the aluminum tube vial cap will slide down the glass vial and melt through the candle wax, destroying the vertical support for the glass vial.

Further, the function of protecting the top of the glass vial from carbon deposits and the colorful appearance of the aluminum tube would be lost. The most practical method to always maintain the aluminum tube vial cap at the top of the glass vial, is to employ a process called "SWEDGING". This is a process where the very end of one opening of the aluminum tube vial cap would be slightly rolled inward to create a stopping point where the aluminum tube vial cap could simply be placed over the glass vial at the top, but not able to slide down as the glass vial and aluminum tube are heated by the lighted candle wick.

There are areas of compensation when comparing the principles of the specialized candle of the present invention to other long lasting candles. Numerous techniques to prolong the burning time life of the fragrance contained in the glass vial were examined. Under the principles and dimensions of the specialized candle of the present invention, there is a limit as to how long the fragrance will last. To investigate the fragrance life of the specialized candle of the present invention, the position of the glass vial in relation to the burning candle wick was tested. Increasing this distance added to the fragrance life but diminished fragrance delivery sand intensity. After numerous methods and experiments, it seemed the only way to lengthen the fragrance life without sacrificing fragrance delivery would be to raise the glass vial slightly higher than the candle wick. In this configuration, a larger portion of the fragrance contained in the glass vial is exposed to the burning candle wick. This configuration increased fragrance life by nearly an hour. Unfortunately, the length of extended glass vial above the candle body top needs to be kept in proper proportion to the corresponding dimensions of the candle. Although the glass vial should always be above the candle's height to function correctly, other techniques were employed to make the candle and the glass vial appear proportionate.

One such method is to remove a portion of the wax from he top of the candle body, within a one inch radius around the exposed candle wick. By removing the wax in this area, the glass vial is still approximately one inch above the candle's height. More of the vial and fragrance are exposed to the burning candle wick because the glass vial is less than an inch away from the exposed candle wick, well within area where the candle wax is removed.

To achieve this method in production, a one-inch radius would have to be drilled out after the candle had set. Again this would be timely and costly. Originally, turning over an already set candle to have the bottom used as the top was considered. The perfectly flush finish of such a candle bottom would be more easily drilled since when most candles are poured the candle tops sag or sink in slightly while setting. After testing the concavity of such setting candle tops, it was discovered that the desired solution for the extension height of the glass vial above the candle top could be readily achieved without any further modification to the candle top.

Referring to the top closure of the glass vial, numerous applications could apply. A material most suited to the overall principles of the specialized candle of the present invention was use of cork to act as a lid or closure for the glass vial. The top of the cork could be decorated for cosmetic appeal. After researching the costs and steps needed to add some type of a decoration to the cork it determined that cork was extremely expensive in relation to all the components used in the specialized candle of the present invention.

The other experimentation for glass vial closure with was a standard perfume sampler closure. These closures are usually a plastic stopper, which functions perfectly well; though it appears like a perfume sampler when it is inserted into the glass vial of the present invention. The small cork used for the closure is far superior to the plastic top. The cork appears natural and is used successfully in many sealing applications worldwide.

A summary of the testing within the given period, the specialized candle of the present invention and its components appear to function desirably. The preferred embodiment of the present invention is a candle two and a half inches tall with a tubular insert placed one-quarter inch away from the centered wick. The tubular insert contains an amount of oils and fragrance that is released or enhanced into the atmosphere, caused by the burning flame of the candle. In the preferred embodiment of this invention, approximately four to five hours of the fragrances maximum scent is achieved once the candle has been lit. This fragrance life depends principally on the fragrance used.

Some candles may vary in the amount of sinking; a not too dramatic situation would occur if another brand candle were to be used. If the depth of the sinking were to change, the remedy would be to adjust the wick length accordingly, as explained above.

The principles of the present invention can be used for candles with multiple glass vials and multiple wicks or multiple glass vials surrounding a single wick. Various cross-sectional candle body geometries also may be employed using the principles of the present invention including, without limitation, triangles or star patterns.

While the principles of the invention have now been made clear in illustrated embodiments, there will be immediately obvious to those skilled in the art, many modifications of structure, proportions, arrangements, the elements, materials, and components used in the practice of the present invention, and otherwise, which are particularly adapted for specific environments and operation requirements without departing from those principles. The appended claims are therefore intended to cover and embrace any such modifications within the limits only of the true spirit and scope of the invention.

I claim:

1. An improved specialized candle, comprising:
   a. an elongated candle body having a top, a bottom, a defined height, and a uniformly defined geometric cross-section;
   b. at least one means for burning said candle body at a predetermined rate;
   c. at least one means for separably containing within said candle body a predetermined fluid without contacting the candle body with said fluid; and
   d. means for disbursing said predetermined fluid as a gas once said means for burning said candle body is engaged.

2. The improved specialized candle as claimed in claim 1 wherein said means for burning said candle body at a predetermined rate further comprises:
   a. a first vertical shaft bored into the top of said candle along the longitudinal central axis thereof to a predetermined depth relative to and less than the overall height of said candle, and having a uniform, predetermined diameter; and
   b. an elongated candlewick inserted into said first vertical shaft, extending along said longitudinal central axis of said candle and extending above the top thereof, and having a uniform, predetermined diameter.

3. The improved specialized candle as claimed in claim 2 wherein said means for separably containing within said candle body a predetermined fluid further comprises:
   a. a second vertical shaft bored into the top of said candle to a predetermined depth relative to and less than the overall height of said candle and at a defined distance from and parallel to said first vertical shaft, and having a uniform, predetermined diameter;
   b. a third vertical shaft having a uniform, predetermined diameter less than said uniform, predetermined diameter of said second vertical shaft, beginning at the bottom of said second vertical shaft and extending through the bottom of said candle;
   c. a receptacle of predetermined length having a closed bottom end, an open top end, a uniform diameter slightly greater than second vertical shaft, inserted into said second vertical shaft and extending a predetermined length above the top of said candle; and
   d. means to close said open top end of said receptacle while said specialized candle is not in use.

4. The improved specialized candle as claimed in claim 3 wherein said means for disbursing said predetermined fluid as a gas once said means for burning said candle body is engaged further comprises:
   a. said receptacle further comprising heat conducting material; and
   b. a sleeve of predetermined length, open at both ends, and having a uniform, predetermined diameter sufficient to snugly fit over the extended top portion of said receptacle wherein the top open end of said sleeve is positionally aligned to be even with the open top end of said receptacle.

5. The improved specialized candle as claimed in claim 4 wherein said predetermined fluid is a fragrant oil.

6. The improved specialized candle as claimed in claim 4 wherein said predetermined fluid is a phenomone.

7. The improved specialized candle as claimed in claim 4 wherein said predetermined fluid is an insect repellent.

8. An improved specialized candle, comprising:
   a. an elongated candle body having a top, a bottom, a defined height, and a uniformly defined geometric cross-section;
   b. a first vertical shaft bored into the top of said candle along the longitudinal central axis thereof to a predetermined depth relative to and less than the overall height of said candle, and having a uniform, predetermined diameter;
   c. an elongated candlewick inserted into said first vertical shaft, extending along said longitudinal central axis of said candle and extending above the top thereof, and having a uniform, predetermined diameter;
   d. a second vertical shaft bored into the top of said candle to a predetermined depth relative to and less than the overall height of said candle and at a defined distance from and parallel to said first vertical shaft, and having a uniform, predetermined diameter;
   e. a third vertical shaft aligned axially with said second vertical shaft, having a uniform, predetermined diameter less than said uniform, predetermined diameter of said second vertical shaft, beginning at the bottom of said second vertical shaft and extending through the bottom of said candle;
   f. a receptacle of predetermined length having a closed bottom end, an open top end, a diameter slightly greater than said second vertical shaft, inserted into said second vertical shaft and extending a predetermined length above the top of said candle;

g. a sleeve of predetermined length, open at both ends, and having a uniform, predetermined diameter sufficient to snugly fit over the extended top portion of said receptacle wherein the top open end of said sleeve is positionally aligned to be even with the open top end of said receptacle;

h. a predetermined volume of desired liquid material within said receptacle; and i. means to close said open top end of said receptacle while said specialized candle is not in use.

9. An improved specialized candle, comprising:

a. an elongated cylindrical candle body having a top, a bottom, a diameter of 2¾ inches, and a height of 2½ inches, and wherein said candle top is concave to a low point of ½ inch from said candle height at the central longitudinal axis of said candle top;

b. a first vertical shaft bored into said candle top along the longitudinal central axis thereof to a depth of 1⅛ inches, and having a uniform, predetermined diameter;

c. an elongated candlewick 1⅝ inches in length inserted into said first vertical shaft, extending along said longitudinal central axis of said candle and extending above the top thereof, and having a uniform, predetermined diameter;

d. a second vertical shaft 7 mm in diameter bored into the top of said candle to a predetermined depth relative to and less than the overall height of said candle at ½ inch from and parallel to said first vertical shaft;

e. a third vertical shaft co-axially aligned with said second vertical shaft, having a uniform diameter of 2 mm, beginning at the bottom of said second vertical shaft and extending through the bottom of said candle;

f. a glass vial of predetermined length having a flat, closed bottom end, an open top end, and a uniform diameter of 8 mm, inserted into said second vertical shaft and extending a predetermined length above the top of said candle and said candlewick;

g. a cylindrical sleeve of predetermined length, with an open bottom end, an open flanged top end, and having a uniform, predetermined diameter sufficient to snugly fit over the extended top portion of said glass vial wherein said open flanged top end of said cylindrical sleeve is positionally aligned to be even with the open top end of said glass vial and to engage said glass vial to prevent said cylindrical sleeve from sliding down said glass vial, and wherein said glass vial has a predetermined exposed length above said candle top and below said sleeve open bottom end;

h. a predetermined volume of predetermined fragrance oil within said glass vial; and i. means to close said open top end of said glass vial while said specialized candle is not in use.

10. The method of manufacturing a fragrant candle comprising the steps:

a. providing a candle body by pouring candle wax into a mold and allowing the wax to set yielding a slightly concave candle top;

b. drilling a first vertical hole into said candle body top along the vertical central longitudinal axis of said candle body, wherein said first vertical hole is less than the height of said candle body;

c. drilling a second vertical hole into said candle body parallel to said first hole, wherein said second vertical hole is less than the height of said candle body;

d. drilling a third vertical hole into central axis of the bottom of said second vertical hole and through the candle bottom, wherein third vertical hole has a diameter less than the diameter of said second vertical hole;

e. inserting a glass vial having a flat closed bottom, an open top, and a diameter slightly larger than said second vertical hole into said second vertical hole until said glass vial flat closed bottom is completely to the bottom of said second vertical hole and said glass vial open top is above said candle top by more than one inch;

f. inserting a candle wick of uniform diameter with a top end and a bottom end into said first vertical hole until said candle wick bottom end is at the bottom of said first hole and said candle wick top end is above said candle top by approximately ½ inch;

g. fitting an aluminum sleeve with and open bottom end and a flanged, open top end on the open to of said glass vial;

h. filling said glass vial with a predetermined fragrance oil; and i. capping said glass vial open end with a removable cork.

* * * * *